United States Patent
Pessin (10) Patent No.: US 8,845,595 B2
(45) Date of Patent: Sep. 30, 2014

(54) DEVICE FOR PROTECTION OF THE NEEDLE FOR A SYRINGE AND INJECTION DEVICE COMPRISING A SYRINGE AND SAID PROTECTION DEVICE

(75) Inventor: Olivier Pessin, Grezieu la Varenne (FR)

(73) Assignee: Tech Group Europe Limited, Dublin (IE)

( * ) Notice: Subject to any disclaimer, the term of this patent is extended or adjusted under 35 U.S.C. 154(b) by 0 days.

(21) Appl. No.: 11/861,567

(22) Filed: Sep. 26, 2007

(65) Prior Publication Data

US 2008/0021409 A1    Jan. 24, 2008

Related U.S. Application Data

(63) Continuation of application No. 10/550,524, filed as application No. PCT/FR2004/000755 on Mar. 25, 2004, now abandoned.

(30) Foreign Application Priority Data

Mar. 25, 2003  (FR) ..................... 03 03657

(51) Int. Cl.
  *A61M 5/32*    (2006.01)
(52) U.S. Cl.
  CPC ..... *A61M 5/3257* (2013.01); *A61M 2005/3247* (2013.01); *A61M 5/3272* (2013.01)
  USPC .......................................... 604/198
(58) Field of Classification Search
  CPC ............. A61M 2005/3247; A61M 2005/3261; A61M 5/3257; A61M 5/326
  USPC .......................... 604/198, 192, 193, 195, 197
  See application file for complete search history.

(56) References Cited

U.S. PATENT DOCUMENTS

| 3,880,163 A | 4/1975 | Ritterskamp |
| 4,631,057 A | 12/1986 | Mitchell |

(Continued)

FOREIGN PATENT DOCUMENTS

| EP | 0904792 A2 | 3/1999 |
| EP | 966 983 A1 | 12/1999 |

(Continued)

OTHER PUBLICATIONS

Int'l Search Report issued Dec. 12, 2012 in Int'l Application PCT/US2012/039385.

(Continued)

*Primary Examiner* — Aarti B Berdichevsky
*Assistant Examiner* — Bradley Osinski
(74) *Attorney, Agent, or Firm* — Panitch Schwarze Belisario & Nadel LLP (57) ABSTRACT

The needle protection device comprises: a protector support (20), defining an introduction duct for a syringe body, a needle protector (22) which may be displaced relative to the protector support (20), between a retracted position and a deployed position, a compression spring (24), applied between the protector support (20) and the needle protector (22) and initial retaining means (38, 40, 54) for the needle protector (22) against the force of the compressed spring (24), said means (38, 40, 54) being released by displacement of the needle protector (22) in a release direction with relation to the protector support (20). The device further comprises mechanical locking means (56) for the needle protector (22) with relation to the protector support (20) in the release direction in the absence of a syringe body in the protector support duct and said mechanical locking means (56) may be deactivated by engaging a syringe body in the duct on the protector support (20).

9 Claims, 6 Drawing Sheets

(56) References Cited

U.S. PATENT DOCUMENTS

| | | |
|---|---|---|
| 4,747,831 A | 5/1988 | Kulli |
| 4,828,548 A | 5/1989 | Walter |
| 4,832,696 A | 5/1989 | Luther et al. |
| 4,871,355 A | 10/1989 | Kikkawa |
| 4,887,998 A | 12/1989 | Martin et al. |
| 4,911,693 A | 3/1990 | Paris |
| 4,923,447 A * | 5/1990 | Morgan ............ 604/198 |
| 4,927,416 A * | 5/1990 | Tomkiel ............ 604/198 |
| 4,931,040 A | 6/1990 | Haber et al. |
| 4,943,282 A | 7/1990 | Page et al. |
| 4,966,592 A | 10/1990 | Burns et al. |
| 4,986,819 A | 1/1991 | Sobel |
| 5,026,349 A | 6/1991 | Schmitz et al. |
| 5,108,378 A | 4/1992 | Firth et al. |
| 5,112,307 A | 5/1992 | Haber et al. |
| 5,141,500 A | 8/1992 | Hake |
| 5,163,918 A * | 11/1992 | Righi et al. ............ 604/198 |
| 5,201,708 A | 4/1993 | Martin |
| 5,201,720 A | 4/1993 | Borgia et al. |
| 5,261,880 A | 11/1993 | Streck et al. |
| 5,267,972 A | 12/1993 | Anderson |
| 5,279,581 A | 1/1994 | Firth et al. |
| 5,346,480 A | 9/1994 | Hess et al. |
| 5,360,410 A | 11/1994 | Wacks |
| 5,380,296 A | 1/1995 | Smedley et al. |
| 5,411,487 A | 5/1995 | Castagna |
| 5,501,672 A | 3/1996 | Firth et al. |
| 5,531,706 A | 7/1996 | de la Fuente |
| 5,558,651 A | 9/1996 | Crawford et al. |
| 5,573,513 A | 11/1996 | Wozencroft |
| 5,591,138 A | 1/1997 | Vaillancourt |
| 5,601,536 A | 2/1997 | Crawford et al. |
| 5,803,918 A | 9/1998 | Vetter et al. |
| 5,817,064 A | 10/1998 | DeMarco et al. |
| 5,891,104 A | 4/1999 | Shonfeld et al. |
| 5,891,105 A | 4/1999 | Mahurkar |
| 5,913,846 A | 6/1999 | Szabo |
| 5,989,226 A | 11/1999 | Hymanson |
| 5,997,513 A | 12/1999 | Smith et al. |
| 6,013,059 A | 1/2000 | Jacobs |
| 6,033,386 A | 3/2000 | Novacek et al. |
| 6,086,566 A | 7/2000 | Arnissolle |
| 6,159,184 A | 12/2000 | Perez et al. |
| 6,171,284 B1 | 1/2001 | Kao et al. |
| 6,186,980 B1 | 2/2001 | Brunel |
| 6,296,625 B1 | 10/2001 | Vetter et al. |
| 6,319,233 B1 | 11/2001 | Jansen et al. |
| 6,319,234 B1 | 11/2001 | Restelli et al. |
| 6,344,032 B1 * | 2/2002 | Perez et al. ............ 604/198 |
| 6,416,323 B1 | 7/2002 | Grenfell et al. |
| 6,475,194 B2 * | 11/2002 | Domici et al. ............ 604/198 |
| 6,547,764 B2 | 4/2003 | Larsen et al. |
| 6,565,540 B1 | 5/2003 | Perouse et al. |
| 6,569,115 B1 | 5/2003 | Barker et al. |
| 6,585,702 B1 | 7/2003 | Brunel |
| 6,613,022 B1 | 9/2003 | Doyle |
| 6,623,459 B1 * | 9/2003 | Doyle ............ 604/197 |
| 6,685,676 B2 | 2/2004 | Jansen et al. |
| 6,719,730 B2 | 4/2004 | Jansen et al. |
| 6,918,889 B1 | 7/2005 | Brunel |
| 6,949,086 B2 | 9/2005 | Ferguson et al. |
| 6,997,901 B2 | 2/2006 | Popovsky |
| 7,029,461 B2 | 4/2006 | Ferguson et al. |
| 7,097,636 B2 | 8/2006 | Pessin |
| 7,144,389 B2 | 12/2006 | Ferguson et al. |
| 7,300,421 B1 | 11/2007 | Lowry et al. |
| 7,429,256 B2 | 9/2008 | Chevallier et al. |
| 7,678,086 B2 | 3/2010 | Chevallier |
| 7,875,006 B2 | 1/2011 | Pessin |
| 7,938,808 B2 | 5/2011 | Pessin |
| 8,118,787 B2 | 2/2012 | Chevallier et al. |
| 8,192,407 B2 | 6/2012 | Pessin |
| 2001/0031949 A1 | 10/2001 | Asbaghi |
| 2001/0039401 A1 | 11/2001 | Ferguson et al. |
| 2002/0002354 A1 | 1/2002 | Vetter et al. |
| 2002/0045864 A1 | 4/2002 | Perez et al. |
| 2002/0068921 A1 | 6/2002 | McWethy et al. |
| 2002/0156426 A1 | 10/2002 | Gagnieux et al. |
| 2002/0193746 A1 | 12/2002 | Chevallier |
| 2003/0050607 A1 | 3/2003 | Gagnieux et al. |
| 2003/0229314 A1 | 12/2003 | McWethy et al. |
| 2004/0015137 A1 | 1/2004 | Hohlfelder et al. |
| 2004/0144668 A1 | 7/2004 | Marshall et al. |
| 2004/0193120 A1 | 9/2004 | Ferguson et al. |
| 2004/0267206 A1 | 12/2004 | Rimlinger et al. |
| 2005/0020985 A1 | 1/2005 | Doyle |
| 2005/0080383 A1 | 4/2005 | Woehr |
| 2005/0119623 A1 | 6/2005 | Pessin |
| 2005/0148933 A1 | 7/2005 | Raven et al. |
| 2005/0148943 A1 | 7/2005 | Chevalier |
| 2005/0165353 A1 | 7/2005 | Pessin |
| 2006/0184133 A1 | 8/2006 | Pessin |
| 2007/0088287 A1 | 4/2007 | Chevallier |
| 2007/0179441 A1 | 8/2007 | Chevallier |
| 2007/0239117 A1 | 10/2007 | Chelak et al. |
| 2008/0208140 A1 | 8/2008 | Barrelle |
| 2008/0294120 A1 | 11/2008 | Chevallier et al. |
| 2008/0312603 A1 | 12/2008 | Chevallier et al. |
| 2009/0105661 A1 | 4/2009 | Chevallier et al. |
| 2010/0217205 A1 | 8/2010 | Chevallier et al. |
| 2012/0095408 A1 | 4/2012 | Eaton et al. |

FOREIGN PATENT DOCUMENTS

| | | |
|---|---|---|
| EP | 1 066 848 A2 | 1/2001 |
| EP | 1474194 A1 | 11/2004 |
| EP | 1532997 A1 | 5/2005 |
| EP | 1235603 B1 | 5/2006 |
| FR | 2653667 A1 | 5/1991 |
| FR | 2762790 A1 | 11/1998 |
| FR | 2 794 650 A1 | 12/2000 |
| FR | 2807665 A1 | 10/2001 |
| FR | 2830764 A1 | 4/2003 |
| FR | 2830765 A1 | 4/2003 |
| FR | 2835753 A1 | 8/2003 |
| FR | 2837107 A1 | 9/2003 |
| FR | 2860162 A1 | 4/2005 |
| FR | 2861598 A1 | 5/2005 |
| FR | 2922455 A1 | 4/2009 |
| JP | H05-500621 T | 2/1993 |
| JP | H08-010324 A | 1/1996 |
| JP | H09-502893 T | 3/1997 |
| JP | 2843677 B2 | 1/1999 |
| JP | 11319090 A | 11/1999 |
| JP | 2003-501218 A | 1/2003 |
| JP | 2003-511106 A | 3/2003 |
| JP | 2004-528075 T | 9/2004 |
| JP | 2005-516741 T | 6/2005 |
| JP | 2006-505340 A | 2/2006 |
| WO | 9426334 A1 | 11/1994 |
| WO | 9835714 A1 | 8/1998 |
| WO | 99 17823 A1 | 4/1999 |
| WO | 0124856 A1 | 4/2001 |
| WO | 0130427 A1 | 5/2001 |
| WO | WO 01 37898 A2 | 5/2001 |
| WO | 0141841 A2 | 6/2001 |
| WO | WO 01 85239 A2 | 11/2001 |
| WO | 02072182 A1 | 9/2002 |
| WO | 02089878 A1 | 11/2002 |
| WO | 03068298 A1 | 8/2003 |
| WO | 03/077977 A2 | 9/2003 |
| WO | 2004043524 A1 | 5/2004 |
| WO | 2004087242 A1 | 10/2004 |
| WO | 2005039678 A2 | 5/2005 |
| WO | 2006/027445 A1 | 3/2006 |

OTHER PUBLICATIONS

Int'l Search Report and Written Opinion issued Dec. 22, 2011 in Intl Application PCT/US2011/031053.
Japanese Office Action mailed Mar. 16, 2010 in JP Appln No. 2006-537346.
Search Report Issued Jul. 9, 2009 in EP Application No. 08 166 632.3.

(56) References Cited

OTHER PUBLICATIONS

Search Report Issued Jun. 13, 2008 in FR Application No. 0758496.
Office Action issued Mar. 22, 2011 in U.S. Appl. No. 12/738,509.
Office Action issued Aug. 25, 2011 in U.S. Appl. No. 12/738,509.
Int'l Search Report issued May 11, 2009 in Int'l Application No. PCT/FR2008/051908; Written Opinion.
Search Report issued Jun. 17, 2008 in FR Application No. 0758497; Written Opinion.
Office Action issued Dec. 23, 2011 in CN Application No. 200880112730.3.
Japanese Office Action mailed Feb. 2, 2010 in Japanese Appln No. 2006-536115.
Office Action Issued Oct. 2, 2008 in U.S. Appl. No. 10/576,938.
Office Action Issued Jul. 21, 2009 in U.S. Appl. No. 10/576,938.
Preliminary Search Report Issued Jun. 21, 2004 in FR Application No. 0312327.
International Search Report and Written Opinion mailed Jun. 6, 2005 in Int'l Application No. PCT/FR2004/002654.
Office Action Issued Dec. 22, 2008 in EP Application No. 04817285.2.
Int'l Preliminary Report on Patentability Issued Jul. 27, 2006 in Int'l Application No. PCT/FR2004/002654.
Office Action dated Mar. 9, 2010 in U.S. Appl. No. 10/576,938.
Office Action issued Sep. 14, 2010 in Japanese Appl Ser No. 2006-536115.
U.S. Appl. No. 14/009,814 by Chevallier, filed Oct. 4, 2013.
Int'l Preliminary Report on Patentability issued Oct. 8, 2013 in Int'l Application No. PCT/US2011/031053.
Office Action issued Dec. 18, 2006 in U.S. Appl. No. 10/507,913 by Pessin.
Office Action issued Sep. 7, 2007 in U.S. Appl. No. 10/507,913 by Pessin.
Office Action issued Dec. 17, 2008 in U.S. Appl. No. 10/507,913 by Pessin.
Office Action issued Oct. 8, 2009 in U.S. Appl. No. 10/507,913 by Pessin.
Office Action issued Apr. 23, 2009 in EP Application No. 04 818 444.4.
Office Action issued Nov. 23, 2010 in EP Application No. 04 818 444.4.
Office Action issued Apr. 17, 2013 in EP Application No. 04 818 444.4.
Int'l Search Report issued Sep. 11, 2003 in Int'l Application No. PCT/FR2003/000722.
Search Report and English translation of Written Opinion issued Jul. 9, 2009 in EP Application No. 08 166 632.3.
Office Action issued Apr. 21, 2005 in U.S. Appl. No. 10/995,035 by Pessin.
Office Action issued Oct. 5, 2005 in U.S. Appl. No. 10/995,035 by Pessin.
Office Action issued Sep. 28, 2010 in JP Application No. 2007-528915.
Office Action issued Sep. 6, 2011 in JP Application No. 2007-528915.
Int'l Search Report issued Jan. 3, 2006 in Int'l Application No. PCT/FR2005/001983.
Int'l Preliminary Report on Patentability issued Feb. 28, 2007 in Int'l Application No. PCT/FR2005/01983.
Int'l Search Report issued Jan. 25, 2006 in Int'l Application No. PCT/FR2005/001926.
Int'l Preliminary Report on Patentability issued Feb. 28, 2007 in Int'l Application No. PCT/FR2005/001926.
Office Action issued May 15, 2009 in U.S. Appl. No. 11/574,333 by Pessin.
Office Action issued Sep. 10, 2008 in U.S. Appl. No. 11/574,333 by Pessin.
Office Action issued Dec. 13, 2007 in U.S. Appl. No. 11/574,333 by Pessin.
Office Action issued Aug. 20, 2010 in U.S. Appl. No. 11/574,176 by Pessin.
Int'l Preliminary Report on Patentability issued Feb. 21, 2006 in Int'l Application No. PCT/FR2004/000755.
Search Report issued Mar. 4, 2004 in FR Application No. 0312642.
Int'l Search Report issued Apr. 4, 2005 in Int'l Application No. PCT/FR2004/002597.
Office Action issued Mar. 11, 2009 in U.S. Appl. No. 10/577,380 by Chevallier.
Office Action issued Feb. 16, 2012 in CN Application No. 200880112413.1.
Search Report and Written Opinion issued Jun. 13, 2008 in FR Application No. 0758495.
Int'l Search Report and Written Opinion issued May 11, 2009 in Int'l Application No. PCT/FR2008/051907.
Int'l Preliminary Report on Patentability issued Jun. 01, 2010 in Int'l Application No. PCT/FR2008/051907.
Office Action issued Mar. 22, 2011 in U.S. Appl. No. 12/738,422.
Int'l Preliminary Report on Patentability issued Dec. 12, 2013 in Int'l Application No. PCT/US2012/039385.
Office Action issued Aug. 18, 2011 in U.S. Appl. No. 12/738,422.
Office Action issued Jul. 1, 2009 in U.S. Appl. No. 12/254,266 by Chevallier.
Office Action issued Feb. 4, 2010 in U.S. Appl. No. 12/254,266 by Chevallier.
Office Action issued Nov. 3, 2011 in U.S. Appl. No. 12/254,266 by Chevallier.
Office Action issued Apr. 23, 2012 in U.S. Appl. No. 12/254,266 by Chevallier.
Office Action issued May 10, 2013 in U.S. Appl. No. 12/254,266 by Chevallier.
Office Action issued Oct. 10, 2013 in U.S. Appl. No. 12/254,266 by Chevallier.
U.S. Application No. 13/666,588 by Feret, filed Nov. 1, 2012.
Int'l Preliminary Report on Patentability issued Jun. 1, 2010 in Int'l Application No. PCT/FR2008/051908.
Search Report issued Jun. 24, 2004 in FR Application No. 0312327.
Office Action issued Sep. 28, 2010 in JP Application No. 2007-528913.
Search Report issued Feb. 22, 2005 in EP Application No. 04 29 2750.
Office Action issued Nov. 28, 2006 in EP Application No. 04 292 750.
Office Action issued Mar. 11, 2008 in EP Application No. 04 292 750.
Office Action issued Sep. 11, 2009 in EP Application No. 05 792 448.
Int'l Preliminary Report on Patentability issued Oct. 17, 2013 in Int'l Application No. PCT/US2011/031053.
Office Action issued Mar. 28, 2007 in U.S. Appl. No. 10/550,524.
Int'l Search Report issued Sep. 22, 2004 in Int'l Application No. PCT/FR2004/000755.
Office Action issued Sep. 1, 2009 in JP Application No. 2006-505752.
Office Action issued Jun. 8, 2010 in JP Application No. 2006-505752.
Office Action issued Dec. 7, 2010 in JP Application No. 2006-505752.

* cited by examiner

DEVICE FOR PROTECTION OF THE NEEDLE FOR A SYRINGE AND INJECTION DEVICE COMPRISING A SYRINGE AND SAID PROTECTION DEVICE

This is a continuation of application Ser. No. 10/550,524 filed Sep. 22, 2005 now abandoned. The entire disclosure of the prior application, application Ser. No. 10/550,524 is hereby incorporated by reference.

The present invention relates to a needle protection device comprising:

a protector support delimiting a passage for accepting a syringe body;

a needle protector able to move with respect to the protector support between a retracted position and a deployed position;

a compression spring pressing between the protector support and the needle protector; and retaining means for initially restraining the needle protector against the action of the compressed spring, which means can be released by moving the needle protector with respect to the protector support in a release direction.

This needle protection device comprises, in the conventional way, a protector support intended to accept the injection syringe. The protector can move with respect to the support under the action of the spring. Retaining means for initially restraining the protector with respect to the support are provided so as to allow the spring to be released only at the end of injection.

These retaining means may be released either automatically at the end of injection, or manually.

When they are being transported, before they are mounted on syringes, the needle protection devices are armed, that is to say that the springs that actuate the protectors are compressed. Thus, should a protection device be vibrated or suffer an impact, the spring may be accidentally released, causing the needle protector to be deployed. The device is then unusable.

It is an object of the invention to propose a needle protection device in which the risks of accidental triggering when a syringe is not present are reduced.

To this end, the subject of the invention is a protection device of this type defined above, characterized in that it comprises mechanical immobilizing means for immobilizing the needle protector with respect to the protector support in the release direction when no syringe body is present in the passage of the protector support, which mechanical immobilizing means can be deactivated by engaging a syringe body in the passage of the protector support.

According to other characteristics of this device, taken in isolation or in any technically feasible combinations:

the mechanical immobilizing means comprise at least one hook secured to a first element chosen from the protector and the support, the or each hook being able to be moved between an immobilizing position in abutment against the second element chosen from the protector and the support when no syringe is present and a mobilizing position away from the second element chosen from the protector and the support when a syringe is present, the or each hook having an actuating face actuated by the syringe body as it is engaged in the passage of the support to move the hook from its immobilizing position to its mobilizing position;

the or each hook has a protrusion projecting into the passage of the protector support when the syringe body is not present;

the or each hook is secured to the needle protector; and the or each hook has a cam surface and the protector support comprises at least one ramp able to collaborate with the or each cam surface to cause the or each hook to become effaced on the outside of the protector support.

A further subject of the invention is an injection device comprising, on the one hand, a syringe which comprises a needle, a tubular body to the distal end of which a needle is fixed, and an injection piston slidably mounted in the body and, on the other hand, a needle protection device as described hereinabove.

The invention will be better understood from reading the description which will follow, given solely by way of example and made with reference to the drawings in which:

FIGS. 11 to 13 illustrate the injection device in the deployed position, FIG. 11 being a view analogous to that of FIG. 8, FIG. 12 being a view in section on the plane XII-XII marked in FIG. 11 and FIG. 13 is a view identical to that of FIG. 11, the syringe not being depicted.

Figure 1:
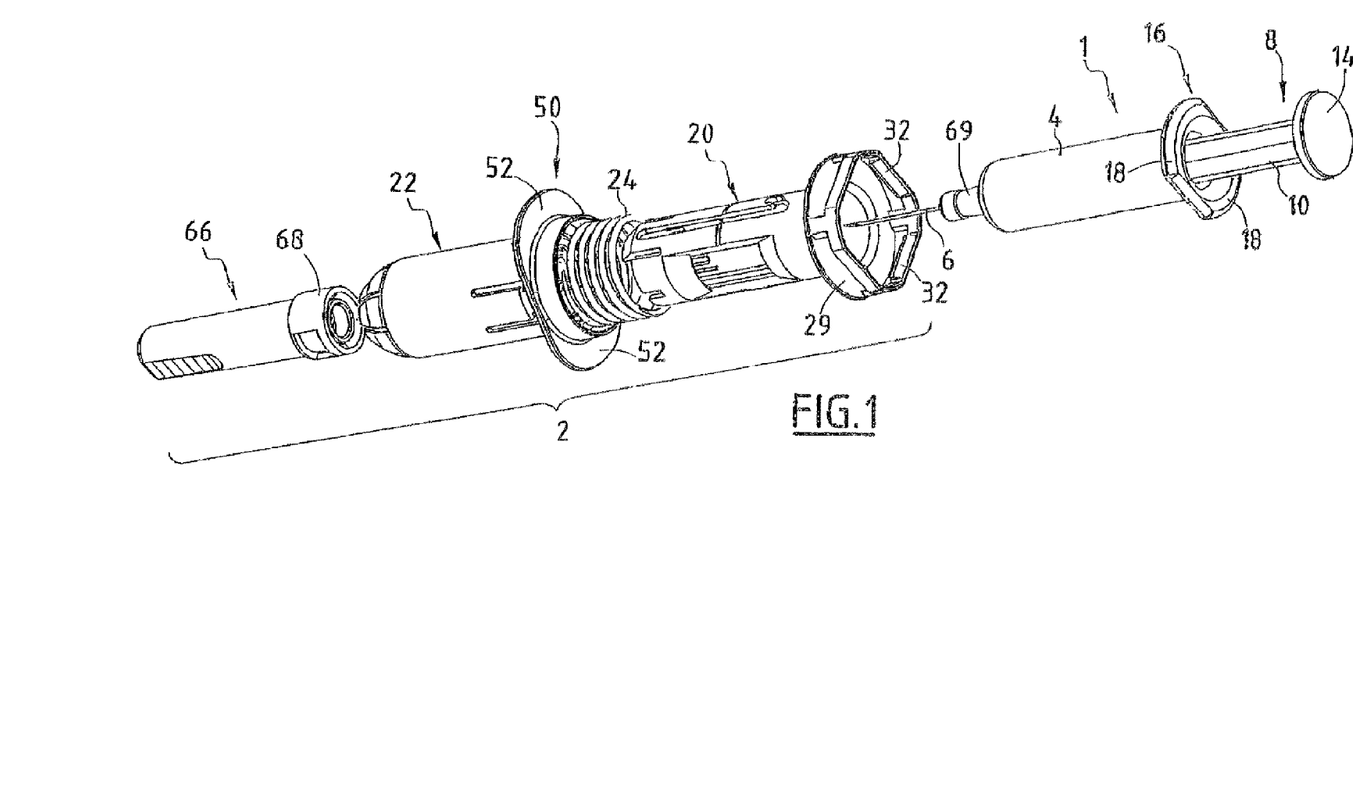
FIG. 1 is an exploded perspective view of an injection device according to the invention, prior to assembly.

FIG. 1 depicts, in perspective, a syringe 1 and a protection assembly 2. In all that which follows, the terms "proximal" and "rear" are synonymous, as are the terms "distal" and "front".

The syringe 1 is a glass syringe of standard format, intended for single use. It contains a liquid to be injected intramuscularly or subcutaneously into a patient. For this purpose it comprises a syringe body or barrel 4, a needle 6 secured to the distal end of the body 4 and a piston 8. This piston in the conventional way comprises a rod 10 provided at its distal end with a plunger 12 visible in FIG. 6A and with a bearing head 14 against which the thumb of the practitioner's hand is intended to bear.

The body 4 of the syringe comprises, in its proximal part, a neck 16 circumferentially delimiting two diametrically opposed lugs 18 intended, normally, particularly when the assembly 2 is not present, to form bearing surfaces for the index and middle finger of the practitioner when he or she is handling the syringe and injecting the liquid located therein.

The protection assembly 2, of overall axis X-X, essentially and as depicted in FIG. 1, comprises:

a support 20 of tubular overall shape;

a protective sleeve 22 arranged coaxially with respect to the support 20 and of a diameter greater than that of the support, and a spring 24.

These three elements will be detailed in succession hereinbelow with reference to FIGS. 2 to 4.

The support 20 comprises a more or less cylindrical main section 26, having an internal diameter more or less equal to the external diameter of the body 4 of the syringe. This section 26 is extended at its proximal end by a secondary section 28 of larger internal and external diameters and those of the main section 26, thereby forming a radial shoulder 29.

The proximal section 28 is provided with means 30 of attachment to the neck of the syringe 16. More specifically, these means 30 comprise diametrically opposed deformable hooks 32, also visible in FIG. 1. Each of these hooks forms a more or less frustoconical ramp surface 32A widening towards the free end of the section 28 which is intended to be pushed back elastically by the lugs 18 of the neck of the syringe 16 when the support 20 is fixed onto the syringe 1. The distance from the hooks 32 to the shoulder 29 is more or less equal to the thickness of the lugs 18. The hooks 32 thus form a means of clipping onto the neck of the syringe 16.

Two crook-shaped through-slots 36 are formed facing one another in the main section 26. Each slot consists of a straight first part 38 which runs more or less along the axis X-X of the support 20 over a length greater than that of the needle 6, and of a straight second part 40, which runs at an angle to the same axis X-X. The inclined part 40 opens into the proximal end of the straight first part 38, forming a V, the vertex of which points toward the proximal end of the assembly 2.

Figures 2, 3, 4, 5:
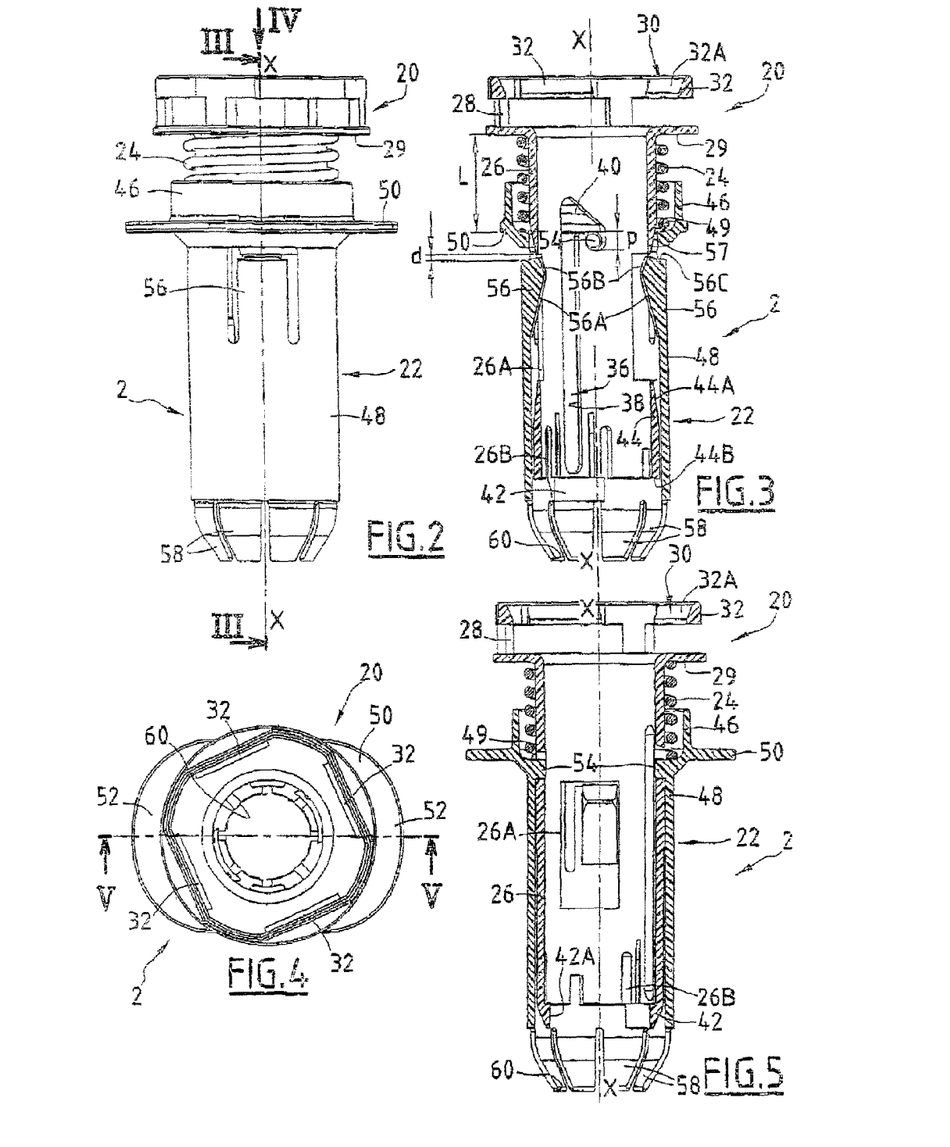
FIG. 2 is an elevation of the protection device belonging to the injection device of FIG. 1, in the retracted position.
FIG. 3 is a view in section on the plane III-III marked in FIG. 2.
FIG. 4 is a view from above in the direction of the arrow IV marked in FIG. 2.
FIG. 5 is a view in section on the plane marked V-V in FIG. 4.

The main section 26 at its distal end comprises a first pair of diametrically opposed elastic tabs 42 each one situated in the continuation of the slots 36 (FIG. 5). These tabs 42 have an internal face 42A of more or less cylindrical shape and an external face 42B that is more or less frustoconical, widening towards the rear end.

The main section 26 comprises a pair of diametrically opposed external ramps 44 situated between the elastic tabs 42 around the circumference of the distal end of this section. They have a more or less frustoconical inclined external surface 44A diverging towards the front end, and a more less flat distal surface 44B. The external surfaces 44A thus face towards the recesses 26A.

Longitudinal recesses 26A are formed in the main section 26 (FIG. 3) at the proximal end of these ramps 44.

Furthermore, on either side of the tabs 42, axial slits 26B are provided originating from the distal end of the support so that before the body 4 of the syringe 1 is inserted in the support 20, these tabs 42 can be deformed radially, particularly inwards.

The protective sleeve 22 is of a length more or less equal to that of the body 4 of the syringe 1. It consists of two cylindrical sections 46 and 48, the main section 46 being of a diameter slightly greater than that of the main section 48. These two sections meet to form a radial shoulder 49.

The sleeve 22 comprises, as an integral part in its proximal part, an external flange 50 in the form of two diametrically opposed lugs 52 (FIG. 4).

Also in its proximal part, but within the protective sleeve 22, two diametrically opposed studs 54 are secured to the sleeve (FIG. 5). These two studs are accommodated and guided in the two slots 36 of the support 20 respectively. The support and the sleeve can thus move one relative to the other in terms of translation along their common axis and in terms of limited rotation about the same axis when the studs lie in the inclined parts 40. The inclined parts 40 therefore form pockets that retain the studs 54, these pockets having a retention depth denoted p in FIG. 3. This depth is measured along the axis of the protector.

Figure 11:
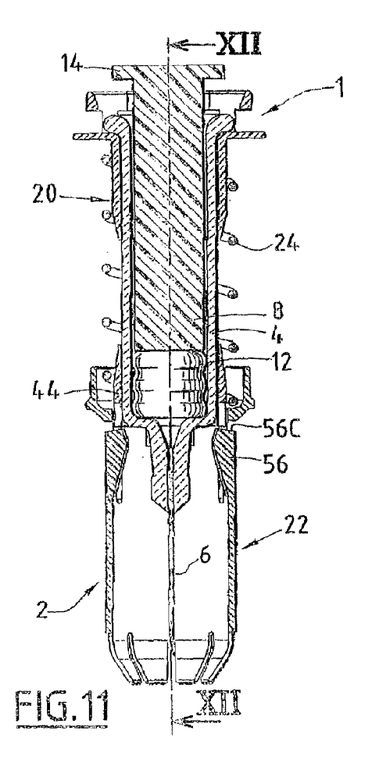
Figure 12:
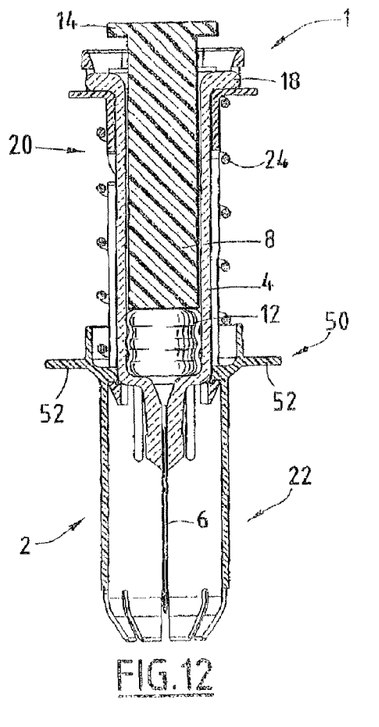
Figure 13:
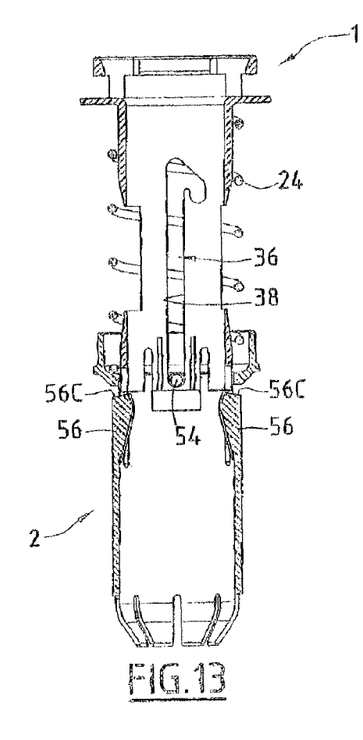

More specifically, the support 20 and the sleeve 22 can move between a position in which the sleeve is retracted, in which position most of the sleeve covers most of the support and the studs 54 lie at the distal end of each of the inclined slot parts 40, as depicted in FIGS. 2 to 7, and a position in which the sleeve is deployed, in which position the sleeve projects axially from the support and the studs lie at the distal end of the straight slot part 38, as depicted in FIGS. 11 to 13.

When the syringe 1 is fixed on the assembly 2, these extreme positions correspond respectively to an injection configuration in which the needle 6 of the syringe 1 is uncovered and intended to be inserted into a patient, and to a protection configuration in which this needle is surrounded by the protective sleeve 22.

The proximal part of the sleeve 22 also internally comprises a pair of diametrically opposed deformable longitudinal hooks 56. These hooks are delimited within the sleeve 22 by lateral slits. These hooks are connected to the sleeve at their distal end. Each hook at its proximal free end has an internal protrusion.

When no syringe is present, and as illustrated in FIG. 3, the external surfaces of the hooks 56 lie in the continuation of the sleeve. By contrast, the internal protrusions of these hooks project inside the cylindrical passage delimited by the sleeve 22. Each protrusion has a front face 56A of more or less frustoconical shape diverging from the axis of the sleeve 22 towards the front. These front faces 56A thus face the front end of the protector.

Each front face 56A is designed to collaborate with an inclined surface 44A formed by the ramps 44 of the support.

Furthermore, each interior protrusion has an inclined rear face 56B facing towards the rear end of the protector and, in particular, towards the two lugs 52. These surfaces 56B are generally frustoconical and diverge from one another towards the rear end of the protector.

The support 20 comprises frustoconical ramps 57 arranged to the rear of the recesses 26A. These ramps are inclined towards the recesses 26A and designed to collaborate with the inclined rear faces 56B.

At its free end, each hook 56 has an inclined transverse surface or 56C forming an end stop.

When there is no syringe present, as illustrated in FIG. 3, the surface 56C of each hook lies immediately facing the corresponding end of the recess 26A. The distance d separating the end face 56C from the edge of the recess is shorter than the depth p of the retention pocket formed of the inclined slot part 40 in which the peg 54 is held.

When the sleeve is in the retracted position, the hooks 56 lie inside the recesses 26A formed in the support 20. When the sleeve is in the deployed position as depicted in FIG. 11, the end faces 56C of the hooks 56 are axially in abutment against the tabs 44, the hooks and tabs thereby providing a rigid immobilization assembly in the deployed position.

The sleeve 22 is also provided at its distal end with a ring of deformable tabs 58, the distal edges of which form a more or less circular opening 60 of a diameter smaller than the internal diameter of the main section 26 of the support 20.

The spring 24 is a spiral-wound spring, located between the protective sleeve 22 and the protector support 20. More specifically, the spring is housed between the shoulder 29 of the support 20 and the shoulder 49 of the sleeve 22. When the sleeve is in the retracted position, the spring 24 is in a compressed state, thus having relaxation energy connected with the stiffness of the spring and with the difference between the length of the spring in the state of rest and its length, marked L in FIGS. 2 to 7, in the compressed state. What this amounts to saying is that the spring 24 exhibits an additional compression force threshold which corresponds to the minimum force needed to compress the spring further from its initial compressed state of FIGS. 2 to 7. The spring stiffness and/or the initial compression length L are chosen so that this force threshold is higher than the pressure force needed to move the piston 8 of the syringe 1 over its entire injection travel. More specifically, the force of the spring in the locked state is greater than the sum of the injection force, that is to say the force needed to expel the liquid from the needle 6 of the syringe 1, and the forces required to overcome the stiction of the plunger 12 and cause it to slide inside the body 4 of the syringe.

Figure 6A:
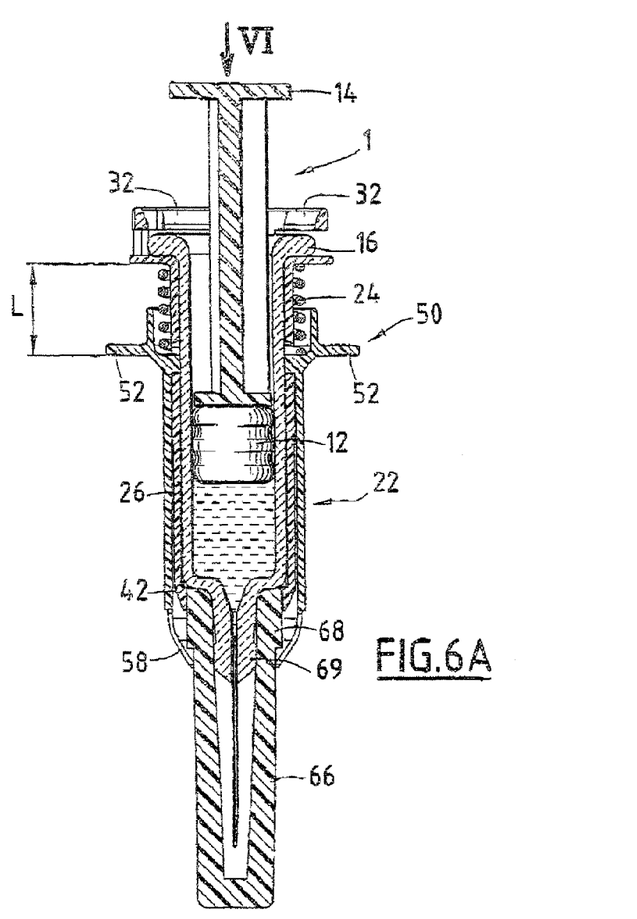
FIG. 6A is a view on the same plane of section as that of FIG. 5, of the injection device according to the invention, prior to use.

As an option, the protection assembly 2 further comprises a cap 66 of tubular overall shape, depicted in FIGS. 1 and 6A.

The cap 66 is designed to surround the needle 6 before the syringe 1 is used. This cap is closed at one of its ends and its opposite end is formed of an annular ring 68 of an outside diameter tailored to be both a match with the surface 42A of the hooks 42 of the support 20 and greater than the diameter of the opening 60 formed by the tabs 58 of the protective sleeve 22. The interior face of this ring 68 is intended to adhere to the glass base 69 of the body of the syringe 4 to which the needle 6 is fixed, particularly with a view to providing a certain seal against bacteria.

The way in which the injection device according to the invention works is as follows:

The protection device 2 is assembled in its retracted configuration, that is to say in its configuration of FIGS. 2 to 7. To do that, the protective sleeve 22 is slipped around the support 20 from the distal end of the support, positioning the spring 24 between them. More specifically, the sleeve is moved axially backwards with respect to the support, at the same time radially deforming the hooks 56 outwards using a suitable tool, this being done at least until these hooks axially reach the front part of the longitudinal recesses 26A. Next, still moving the sleeve backwards, the pegs 54 are pressed against the external surfaces 42B of the tabs 42, deforming the latter inwards until the pegs are housed in the slot parts 38. The rearwards movement of the protector 22 then continues until the studs 54 are housed in the inclined slot parts 40, causing the support and the protector to pivot one with respect to the other. The protector is thus in the retracted position.

In this position and as illustrated in FIG. 3, the internal protrusions of the hooks 56 project into the passage for accepting the syringe so that the rear transverse surface 56C lies immediately in front of the corresponding edge of the recess 26A.

The end surface forms an end stop able to collaborate with the edge of the recesses 26A to prevent the protective sleeve 22 from retreating towards the rear end of the support 20. The hooks 56 are therefore in the immobilizing position.

As will be explained later on, in as much as the retention of the spring that moves the protective sleeve is released by moving the protector rearwards, any risk of accidental triggering of the protective sleeve while the protective device is being transported is avoided because the protective sleeve is immobilized in its release direction independently of the spring retention means, as long as no syringe has been introduced into the protector support.

The glass syringe 1 is prefilled with a liquid to be injected into a patient. This syringe is equipped with the cap 66 which grips onto the base 57 of the syringe body 4.

Figure 6B:
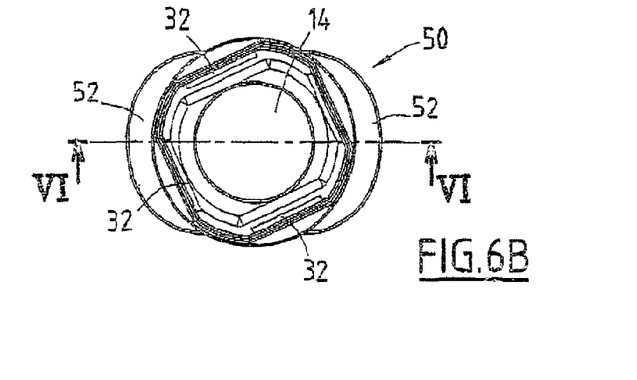
FIG. 6B is a view from above in the direction of the arrow VI marked in FIG. 6A.

The syringe and the cap are inserted inside the assembly 2 to form the injection device, as depicted in FIGS. 6A and 6B. More specifically, the body 4 of the syringe is moved more or less axially within the support 20. As the body 4 of the syringe engages in the support 20, and as illustrated in FIG. 6A, the syringe body presses against the inclined rear faces 56B, thus causing the protrusions of the hooks 56 to become effaced towards the outside.

In particular, the end faces 56C of the hooks and the corresponding edges of the recesses 26A are misaligned. The hooks are therefore in the mobilizing position.

The syringe body is moved within the protector until the neck of the syringe 16, indexed by the projections 34, clips inside the proximal section 28, deforming the hooks 32 radially outwards. The lugs 18 of the neck of the syringe 16 are then retained axially by the hooks 32, while the peripheral protrusions 34 restrain the neck of the syringe, and therefore the syringe, in terms of rotation relative to the support 20.

In addition, in as much as the neck of the syringe 16 is completely clipped inside the section 28, it can no longer fulfill its usual role of forming a bearing surface for the practitioner's index and middle fingers. This bearing function is performed by the flange 50 secured to the sleeve 22. Specifically, in as much as the length of the protective sleeve 22 is more or less equal to that of the syringe body 4 and/or in as much as the flange 50 is formed at the proximal end of this sleeve, the practitioner can then handle the syringe by resting his thumb on the bearing head 14 of the piston 8, as usual, and resting his index and middle fingers against the faces of the lugs 52 facing towards the needle 6.

Furthermore, when the syringe 1 is fixed on the protector support 20 as depicted in FIGS. 6A and 6B, the cap 66 projects out from the protective sleeve 22.

When the practitioner is ready to inject the liquid contained in the syringe, he withdraws the cap 66 by pulling it axially forwards. The ring 68 then moves over the opening 60, deforming the tabs 58. Once the cap 66 has been withdrawn, the tabs 58 return to their initial position. The passage hole 60 at the distal end of the sleeve, of a diameter smaller than the outside diameter of the cap 66, then prevents the cap from being refitted around the needle. The collaboration between the cap 66 and the tabs 58 therefore forms a way of checking that the injection device is indeed being used for the first time.

Figure 7:
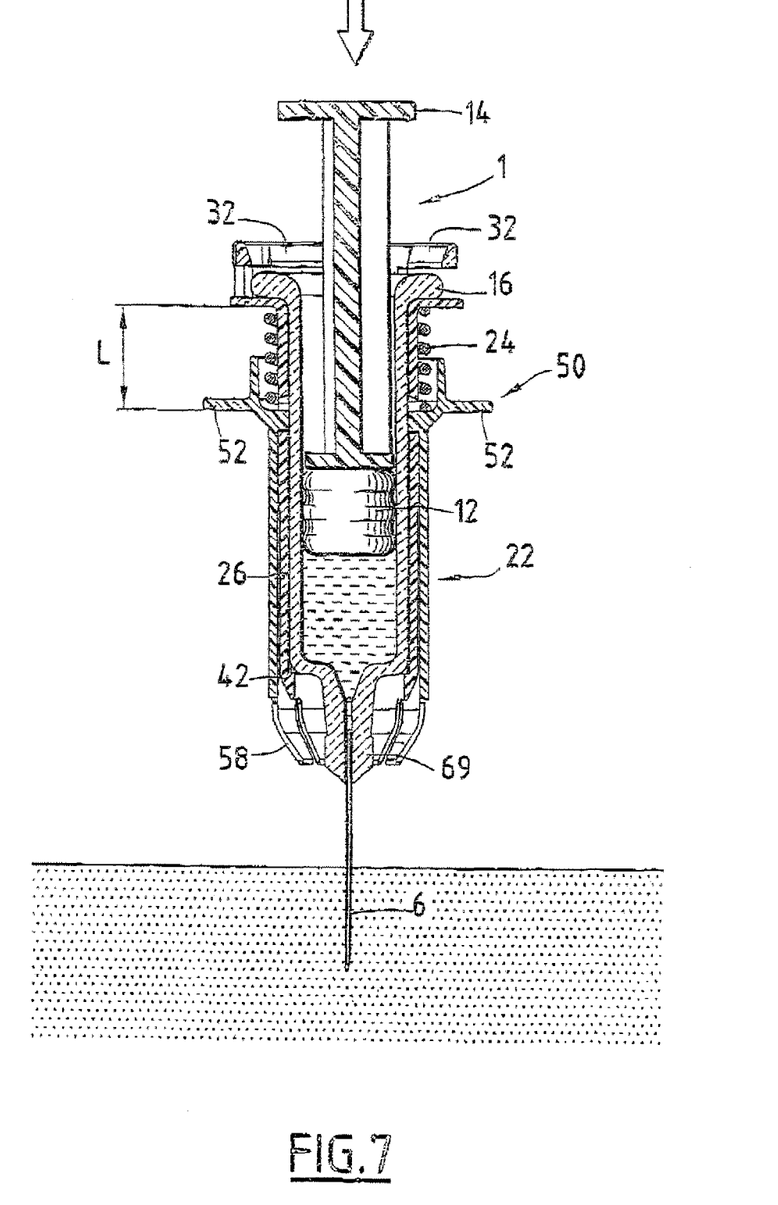
FIG. 7 is a view analogous to that of FIG. 6A, the injection device being in the process of being used.

The practitioner then pierces the patient's skin with the needle 6. He injects the liquid contained in the syringe by pressing against the bearing head 14 of the piston 8, his index and middle fingers remaining in contact with the faces of the lugs 52 that face towards the needle. During injection, there is no movement between the protector support 20 and the protective sleeve 22, the spring 24 remaining compressed at a length L, as depicted in FIG. 7.

Injection continues until the plunger 12 of the piston 8 reaches the end of the injection travel.

Figure 8:
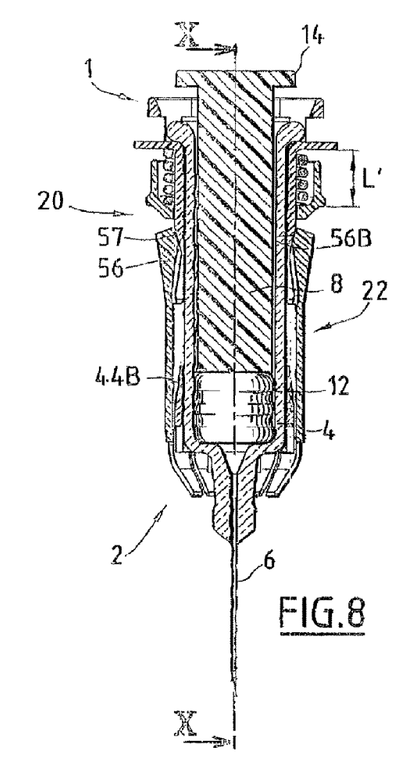
FIG. 8 is a view on the same plane of section as that of FIG. 3, of the injection device at the end of use.
Figure 9:
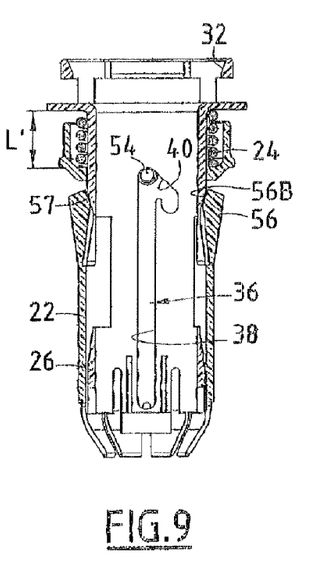
FIG. 9 is a view identical to that of FIG. 8, the syringe of the injection device not being depicted.
Figure 10:
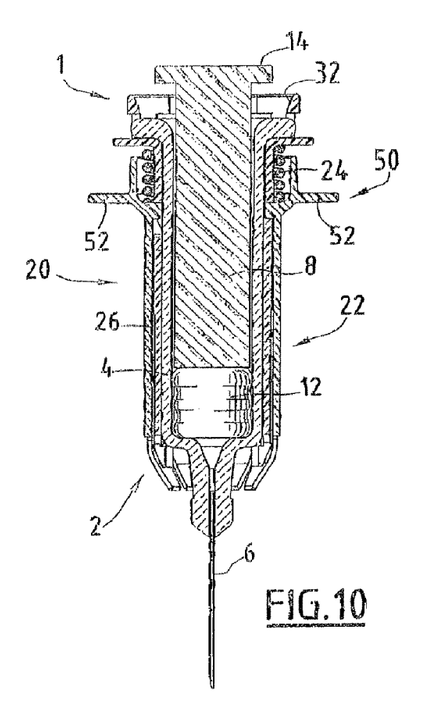
FIG. 10 is a view in section on the plane X-X marked in FIG. 8.

The practitioner then withdraws the needle from the patient. In order to trigger the protection assembly 2, the practitioner exerts additional pressure on the piston rod 8. This pressure needs to exceed the predetermined force produced by the spring 24 in the locked state so that this spring is compressed further and changes from its length L to a shorter length L', as depicted in FIGS. 8 to 10. To do this, on the assumption that the syringe support does not move, the protective sleeve 24 moves axially towards the proximal end of the support 20. The practitioner performs this movement by exerting corresponding pressure with his index and middle fingers on the lugs 52 of the flange 50 of the sleeve 22. This pressure, combined with the translational movement, causes the protective sleeve 22 to rotate about the syringe support 20, the studs 54 being guided by the inclined slot parts 40. This rotational movement continues until the studs reach the proximal end of this slot part 40, that is to say the proximal end of the longitudinal slot part 38, as visible in FIG. 9. The device 2 is then in the position in which the spring 24 is unlocked.

The movement of the needle protector towards the rear end of the support in the spring release direction is rendered possible by the collaboration between the inclined rear faces 56B of the protrusions of the hooks and the ramps 57. During the movement of the protector, additional outwards deformation of the hooks occurs as illustrated in FIG. 8. Thus, the hooks part from one another to pass over the exterior surface of the protective sleeve beyond the recesses 26A.

The practitioner then releases the pressure he was hitherto exerting on the flange 50, allowing the spring 24 to relax to a state of rest. The studs 54 move translationally inside the longitudinal slot part 38, as far as the distal end thereof as depicted in FIG. 13. The translational movement of the protective sleeve 22 relative to the support 20 can be controlled by the practitioner, if the latter releases gradually the retention that he is exerting with his fingers on the flange 50. When the studs 54 have reached the distal end of the slot 36 (FIG. 13) the protector is in its deployed position.

Furthermore, when the protective sleeve 22 is in translational movement relative to the support 20, the hooks 56 enter the longitudinal recesses 26A of the support until they slide along the distal ramps 44 of the support, through the collaboration of their complementary surfaces 56A and 44A.

When the protector is in the deployed position, the hooks 56 are held by collaboration of the surfaces 56C and 44B so that the protective sleeve 22 cannot be returned to its initial position. Likewise, the sleeve 22 cannot be readily torn from the support 20 because the studs 54 are in abutment against the distal end of the longitudinal slot part 38 (FIG. 13), the tabs 42 forming this end being held radially between the body of the syringe 1 and the protective sleeve 22.

The injection device according to the invention is thus simple to use, while at the same time allowing the practitioner to control the movement whereby the needle is covered by the protective sleeve. The number of parts of which the protection assembly 2 depicted is formed is reduced to three.

The device according to the invention can be fitted to various types of syringe, these varying both in terms of their shape and in terms of their volume. This device therefore has the advantage of not calling into question the overall shape of the syringes used and therefore leads to no modification to the industrial methods used to fill these syringes.

Various variants of the device according to the invention are conceivable:
- unlike in the exemplary embodiment described hereinabove, the studs 54 and/or the flange 50 of the protective sleeve 22 may be attached to the sleeve 22 rather than formed as an integral part thereof;
- as the inverse of the device described, the studs 54 may be produced on the external surface of the protector support 20 and the guide slot 36 may be formed in the protective sleeve 22;
- the support 20 may be made of one piece with the syringe body 4; and/or
- the protrusions 34 of the means 30 for fixing the support 20 on the neck of the syringe 16 may be omitted and possibly replaced by one or more hooks similar to the hooks 32 described hereinabove, all of these hooks axially retaining the neck 16 with respect to the support 20 for any relative angular position of the syringe 1 with respect to support; in this case, the syringe 1 is free to turn inside the support 20, and this in turn provides greater ease of attachment of the protective assembly 2 to the syringe (absence of indexing).

The invention claimed is:

1. A needle protection device comprising:
a protector support (20) delimiting a syringe barrel (4);
a needle protector (22) able to move with respect to the protector support (20) between a retracted position and a deployed position;
a compression spring (24) pressing between the protector support (20) and the needle protector (22);
at least one stud (54) of the needle protector (22) retained within at least one opposing slot (38, 40) in the protector support (20), configured for initially restraining the needle protector (22) against the action of the compressed spring (24) in the retracted position, and wherein said needle protector (22) is releasable by moving the needle protector (22) with respect to the protector support (20) in a release direction;
at least one hook (56) secured to the needle protector (22) or the protector support (20) and engageable with the other of the needle protector (22) and the protector support (20) for immobilizing movement of the needle protector (22) with respect to the protector support (20) in the release direction when no syringe barrel (4) is present in the passage of the protector support; and
said at least one hook (56) is deformable by engaging a syringe barrel (4) in the passage of the protector support (20) for deactivating the immobilization of the needle protector (22).

2. The needle protection device as claimed in claim 1, wherein the at least one hook (56) includes an actuating face (56B), and is deformable between an immobilizing position in abutment against a portion of the needle protector (22) or the protector support (20) when no syringe (1) is present in the passage of the protector support (20) and a mobilizing position away from the portion of the needle protector (22) or the protector support (20) when a syringe (1) is present in the passage of the protector support (20), wherein the actuating face (56B) is actuated by the syringe barrel (4) as it is engaged in the passage of the protector support (20) to move the at least one hook (56) from its immobilizing position to its mobilizing position.

3. The needle protection device as claimed in claim 2, wherein the at least one hook (56) is secured to the needle protector (22).

4. The needle protection device as claimed in claim 3, wherein the at least one hook (56) includes a protrusion projecting into the passage of the protector support (20) when the syringe barrel (4) is not present in the passage of the protector support (20).

5. The needle protection device as claimed in claim 3, wherein the actuating face (56B) has a cam surface and the protector support (20) comprises at least one ramp (57) able to collaborate with the cam surface (56B) to cause the at least one hook (56) to become effaced on the outside of the protector support (20).

6. The needle protection device as claimed in claim 2, wherein the protector support (20) comprises a distal surface (44B) able to collaborate with the at least one hook (56) to keep the needle protector (22) in the deployed position.

7. The needle protection device of claim 1, wherein the at least one stud of the needle protector (22) remains in the opposing slot in the retracted position upon deactivation of the immobilization of the needle protector (22), and wherein subsequent manual movement of the needle protector (22) with respect to the protector support (20) in the release direction by a user is required to release the needle protector (22) from the retracted position to the deployed position.

8. An injection device comprising, a syringe (1) which comprises a needle (6), a tubular barrel (4), a distal end of the tubular barrel (4) having the needle (6) fixed thereto, and an injection piston (8) slidably mounted in the tubular barrel (4) the syringe (1) being positioned in the protector support (20) of the needle protection device (2) of claim 1.

9. A needle protection device comprising:
- a protector support (20) defining a passage for receiving a syringe barrel (4);
- a needle protector (22) moveable with respect to the protector support (20) between a retracted position and a deployed position;
- a compression spring (24) pressing between the protector support (20) and the needle protector (22);
- at least one stud (54) of the needle protector (22) retained within at least one opposing slot (38, 40) in the protector support (20), configured for restraining the needle protector (22) against the action of the compressed spring (24) when the needle protector (22) is in the retracted position, thereby preventing the needle protector (22) from moving from the retracted position to the deployed position, and wherein said needle protector (22) is releasable by moving the needle protector (22) with respect to the protector support (20) in an upward release direction opposite the action of the compressed spring (24); and
- at least one hook (56) of the needle protector (22) configured to:
  - immobilize the needle protector (22) in the upward release direction when the needle protector (22) is in the retracted position and no syringe barrel (4) is present in the passage of the protector support (20), said at least one hook (56) being deformable by engaging a syringe barrel (4) advanced into the passage of the protector support (20) to deactivate the immobilization of the needle protector (22), and
  - prevent return of the needle protector (22) to the retracted position when the needle protector (22) is in the deployed position.

* * * * *